United States Patent [19]

Culbert

[11] Patent Number: Plant 5,490

[45] Date of Patent: Jun. 11, 1985

[54] CHRYSANTHEMUM PLANT — NAMED ILLINI MIST

[75] Inventor: John R. Culbert, Clinton, Ill.

[73] Assignee: University of Illinois, Chicago, Ill.

[21] Appl. No.: 488,072

[22] Filed: Apr. 25, 1983

[51] Int. Cl.[3] ..... A01H 5/00

[52] U.S. Cl. ..... Plt./74

[58] Field of Search ..... Plt./74

*Primary Examiner*—Robert E. Bagwill

*Attorney, Agent, or Firm*—Schwartz, Jeffery, Schwaab, Mack, Blumenthal & Koch

[57] ABSTRACT

A new and distinct form of chrysanthemum plant named Illini Mist characterized by its flat capitulum form and single capitulum type; pink tubular shaped spoon tipped ray florets, 60–70 mm. diameter across face of capitulum, excellent flower production, and its short and compact growth habit.

1 Drawing Figure

The present invention comprises a new and distinct cultivar of *Chrysanthemum morifolium,* Ramat., named Illini Mist.

Illini Mist is a product of a planned breeding program which had the objective of creating new chrysanthemum cultivars with single anemone capitulum type, pink ray color and tubular ray floret form, 8 week response, and with the ability to produce commercially acceptable quality in year round pot mum programs. Such traits in combination were not present in previously available commercial cultivars.

Illini Mist was originated from a hybridization made in a controlled breeding program in Urbana, Ill. in 1976. The female parent was identified as 68-04-73 and the male parent as 21-04-74. Illini Mist was discovered and selected as one flowering plant within the progeny of the selected parentage by John R. Culbert in June, 1977 in a controlled environment at Urbana, Ill., and subsequently given the code name FP ILL 76-99.

The first act of asexual reproduction of Illini Mist was accomplished when vegetative cuttings were taken from the initial selection in September, 1977 in a controlled environment in Urbana, Ill. by a technician working under formulations established and supervised by John R. Culbert. Horticultural examination of selected units initiated Dec. 18, 1977 has demonstrated that the combination of characteristics as herein disclosed for Illini Mist are firmly fixed and are retained through successive generations of asexual reproduction.

Illini Mist has not been observed under all possible environmental conditions. The phenotype may vary significantly with variations in environment such as temperature, light intensity, and day length. The following observations, measurements and comparisons describe plants grown in Urbana and West Chicago, Ill., and Parrish, Fla. under greenhouse conditions which approximate those generally used in commercial practice.

The following traits have been repeatedly observed and are determined to be basic characteristics of Illini Mist, which in combination distinguish this chrysanthemum as a new and distinct cultivar:

1. Flat capitulum form.
2. Single capitulum type.
3. Ray florets nearly tubular with only a tiny spoon tip.
4. Ray florets have bright pink spoon tips and light pink tubes.

5. Yellow-green (immature) to yellow (mature) disc floret.
6. Diameter across the face of the capitulum 60–70 mm.
7. Short pot plant height of about 200 mm. from edge of pot.
8. Semi-upright branching pattern and compact growth habit.
9. Excellent flower production.

Of the many commercial cultivars known to the present inventor, the most similar in comparison to Illini Mist is Fantasy, disclosed in U.S. Plant Pat. No. 4,469 granted Oct. 23, 1979. In comparison to Fantasy, Illini Mist is more compact, performs better under high temperatures, and its ray florets are almost completely tubular with only a tiny spoon tip whereas the ray florets of Fantasy have much larger spoon tips. The capitulum form and color are similar to those same characteristics of Fantasy.

The accompanying color photographic drawing shows typical inflorescence and foliage characteristics of Illini Mist, with colors being as nearly true as possible with illustrations of this type.

In the following description color references are made to The Royal Horticultural Society Colour Chart. The color values were determined between 9:00–9:30 A.M. on Apr. 25, 1983 under 2000–2500 foot candles light intensity at Parrish, Fla.

Classification:

*Botanical.*—*Chrysanthemum morifolium,* Ramat., cv ILLINI MIST.

*Commercial.*—Novelty Daisy Pot Mum.

INFLORESCENCE

A. Capitulum:

*Form.*—Flat, single, spooned; very long tubular handles and tiny, short spoon tips, with regular arrangement of ray florets and slight spacing between each floret; 30–35 ray florets depending on season and culture.

*Type.*—Daisy.

*Diameter across face.*—60–70 mm.

*Number.*—Normally 18 to 20 per plant grown in sprays on pinched plants.

B. Corolla of ray florets:

*Color (general tonality from a distance of three meters.*—Bright pink; good color retention.

*Color* (*abaxial*).—75B.

*Color* (*adaxial*).—Spoon 70B, tube 70C-D, fading to an even lighter color approaching white under conditions of advanced aging and high temperature.

C. Corolla of disc florets:

*Color* (*mature*).—Yellow.

*Color* (*immature*).—Yellow-green.

D. Reproductive organs:

*Androecium.*—Present disc florets only — many.

*Gynoecium.*—Present ray florets and disc florets — one per floret.

PLANT

A. General appearance: Short, compact and slightly spreading but upright growth habit; abundant foliage; 200 mm. plant height.

B. Foliage:

*Color* (*abaxial*).—147B.

*Color* (*adaxial*).—147A.

*Shape.*—Deeply lobed and slightly serrated.

C. Response: Early, generally 8 weeks.

I claim:

1. A new and distinct form of chrysanthemum plant named Illini Mist, as described and illustrated, and particularly characterized by its flat capitulum form and single capitulum type; pink tubular shaped spoon tipped ray florets; 60–70 mm. diameter across face of capitulum; excellent flower production, and its short and compact growth habit.

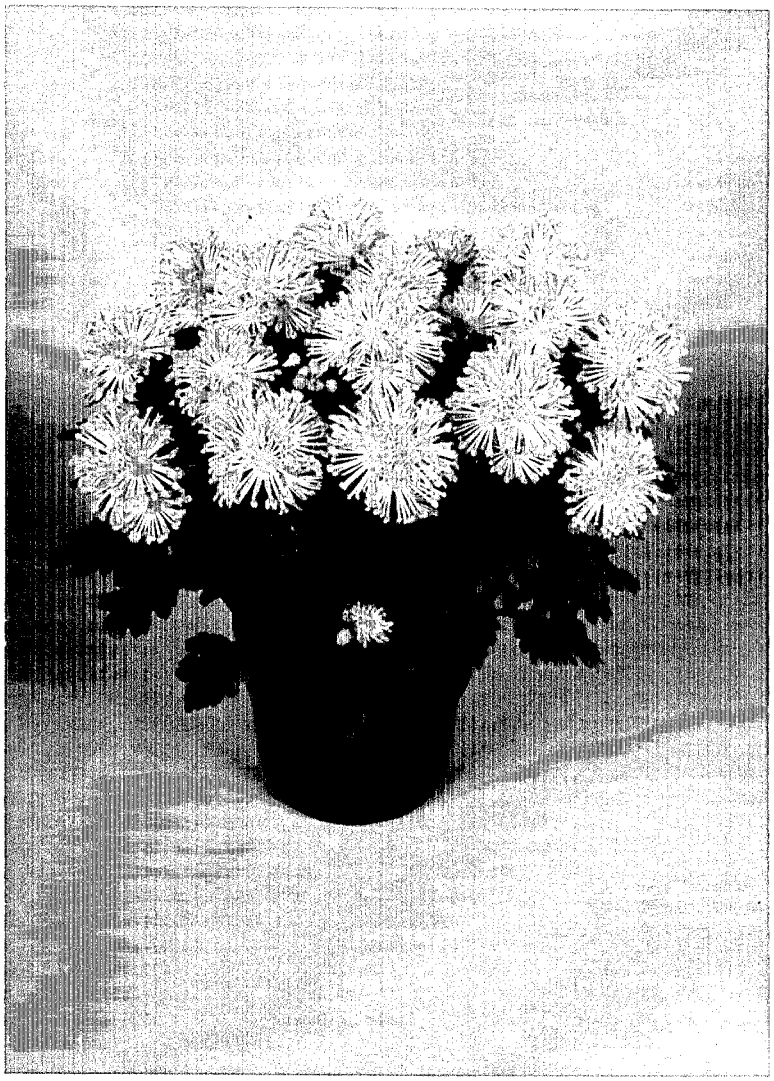

* * * * *